US012163970B2

(12) United States Patent
Blakeslee et al.

(10) Patent No.: US 12,163,970 B2
(45) Date of Patent: Dec. 10, 2024

(54) SYSTEM AND METHOD FOR INSPECTING A COMPONENT FOR ANOMALOUS REGIONS

(71) Applicant: Raytheon Technologies Corporation, Farmington, CT (US)

(72) Inventors: Brigid A. Blakeslee, Hamden, CT (US); Francesca Stramandinoli, West Hartford, CT (US); Amit Surana, Newington, CT (US); Mahmoud El Chamie, Rocky Hill, CT (US); Ozgur Erdinc, Mansfield, CT (US)

(73) Assignee: RTX CORPORATION, Farmington, CT (US)

( * ) Notice: Subject to any disclaimer, the term of this patent is extended or adjusted under 35 U.S.C. 154(b) by 252 days.

(21) Appl. No.: 17/744,223

(22) Filed: May 13, 2022

(65) Prior Publication Data

US 2023/0366896 A1    Nov. 16, 2023

(51) Int. Cl.
*G01N 35/00* (2006.01)
*G01D 11/28* (2006.01)
(Continued)

(52) U.S. Cl.
CPC ......... *G01N 35/0099* (2013.01); *G01D 11/28* (2013.01); *G01N 21/8851* (2013.01); *G01N 2021/8854* (2013.01); *G01N 33/2045* (2019.01)

(58) Field of Classification Search
CPC ........... G01N 35/0099; G01N 21/8851; G01N 33/2045; G01N 2021/8854; G01D 11/28;
(Continued)

(56) References Cited

U.S. PATENT DOCUMENTS 8,223,327 B2   7/2012  Chen et al.
9,816,939 B2  11/2017  Duffy et al.
(Continued)

FOREIGN PATENT DOCUMENTS

CN    106780455   12/2016
CN    110211112    9/2019
WO   2019177539    9/2018

OTHER PUBLICATIONS

Blakeslee et al., "Selective and hierarchial allocation of sensing resources for anomalous target identification in exploratory missions", 2021 IEEE International Symposium on Safety, Security, and Rescue Robotics, Oct. 25, 2021, pp. 196-203.
(Continued)

*Primary Examiner* — Hung V Nguyen
(74) *Attorney, Agent, or Firm* — Carlson, Gaskey & Olds, P.C.

(57) ABSTRACT

A method of inspecting a component for anomalous regions includes recording a plurality of sensor readings using one or more sensors, each reading corresponding to a different region of the component; determining an appearance metric for each reading; and determining a nominal appearance metric based on individual values of the appearance metric for a first subset of the readings. The method includes, for a particular sensor reading outside the first subset: determining a difference between the nominal appearance metric and the appearance metric of the particular sensor reading; updating the nominal appearance metric based on the particular sensor reading; and, based on the difference exceeding a threshold: determining that the particular sensor reading is anomalous and corresponds to an anomalous region of the component, and recording additional sensor readings of the anomalous region using one or more sensing parameters
(Continued)

that differ from those used to record the anomalous sensor reading.

24 Claims, 4 Drawing Sheets

(51) Int. Cl.
    *G01N 21/88*     (2006.01)
    *G01N 33/2045*     (2019.01)

(58) Field of Classification Search
    CPC .. G05B 23/0235; G06T 7/0008; G06T 7/0004
    See application file for complete search history.

(56) References Cited

U.S. PATENT DOCUMENTS

| | | | |
|---|---|---|---|
| 9,976,967 B2 | 5/2018 | Bense et al. | |
| 10,393,671 B2 | 8/2019 | Thattaisundaram et al. | |
| 10,861,148 B2 * | 12/2020 | Wang | G06T 7/0006 |
| 2019/0285980 A1 | 9/2019 | Yoshikawa | |

OTHER PUBLICATIONS

European Search Report for European Patent Application No. 23171695.2 dated Oct. 18, 2023.

* cited by examiner

SYSTEM AND METHOD FOR INSPECTING A COMPONENT FOR ANOMALOUS REGIONS

BACKGROUND

This application relates to component inspection, and more particularly to a system and method for inspecting a component for anomalous regions.

Defects are of concern for parts undergoing maintenance and repair, as well as for new parts, as defects may accumulate during manufacturing processes/operations, resulting in rework, scrap, or costly post-process inspection. Human inspection may result in errors due to subjectivity or fatigue, and may also be potentially ergonomically taxing.

Although some autonomous visual inspection systems are known, such systems are limited by predefined libraries or labeled training data and are not robust to changes in environment or defect appearance, and may require significant modification when being redeployed for other tasks. This limits versatility, constraining an implementation to a specific, limited set of defects and/or controlled environmental conditions.

SUMMARY

A method of inspecting a component for anomalous regions according to an example embodiment of the present disclosure includes recording a plurality of sensor readings for a component using one or more sensors, each sensor reading corresponding to a different region of the component; determining an appearance metric for each of the sensor readings; and determining a nominal appearance metric based on individual values of the appearance metric for a first subset of the sensor readings. The method also includes, for a particular sensor reading of the plurality of sensor readings that is outside of the first subset: determining a difference between the nominal appearance metric and the appearance metric of the particular sensor reading; updating the nominal appearance metric based on the particular sensor reading; and, based on the difference exceeding a threshold: determining that the particular sensor reading is an anomalous sensor reading that corresponds to an anomalous region of the component, and recording additional sensor readings of the anomalous region using one or more different sensing parameters that differ from those used to record the anomalous sensor reading.

In a further embodiment of the foregoing embodiment, the one or more sensors include a camera.

In a further embodiment of any of the foregoing embodiments, the one or more different sensing parameters include an imaging resolution of the at least one sensor.

In a further embodiment of any of the foregoing embodiments, the one or more sensors include a first sensor and a second sensor, and said recording a plurality of sensor readings is performed using the first sensor. The method includes moving the first sensor relative to the component along a path to position the first sensor for said recording a plurality of sensor readings; and using a second sensor, which is separate from the first sensor, for said recording additional sensor readings while the first sensor continues to follow the path.

In a further embodiment of any of the foregoing embodiments, the first and second sensors are both cameras.

In a further embodiment of any of the foregoing embodiments, one of the first and second sensors is a camera, and the other of the first and second sensors is a depth sensor, an ultrasonic sensor, or an x-ray imaging device.

In a further embodiment of any of the foregoing embodiments, said moving the first sensor relative to the component includes using a set of one or more robotic arms, a snake-arm robot, or a drone to move the first sensor relative to the component.

In a further embodiment of any of the foregoing embodiments, the one or more different sensing parameters include one or more of: a position of the sensor relative to the component, a distance between the sensor and the component, or an angle of the sensor relative to the component.

In a further embodiment of any of the foregoing embodiments, the one or more different sensing parameters include one or more of: a position of a light source relative to the component, an orientation of the light source relative to the component, or a brightness of the light source.

In a further embodiment of any of the foregoing embodiments, said updating the nominal appearance metric includes the nominal appearance metric based on the appearance metric of the particular sensor reading and M most recent sensor readings that precede the particular sensor reading.

A system for inspecting a component for anomalous regions according to an example embodiment of the present disclosure includes one or more sensors and processing circuitry. The processing circuitry is configured to record a plurality of sensor readings for a component using the one or more sensors, each sensor reading corresponding to a different region of the component; determine an appearance metric for each of the sensor readings; and determine a nominal appearance metric based on individual values of the appearance metric for a first subset of the sensor readings. The processing circuitry is also configured to, for a particular sensor reading of the plurality of sensor readings that is outside of the first subset, determine a difference between the nominal appearance metric and the appearance metric of the particular sensor reading; update the nominal appearance metric based on the particular sensor reading; and based on the difference exceeding a threshold: determine that the particular sensor reading is an anomalous sensor reading that corresponds to an anomalous region of the component, and record additional sensor readings of the anomalous region using one or more different sensing parameters that differ from those used to record the anomalous sensor reading.

In a further embodiment of the foregoing embodiment, the one or more sensors include a camera.

In a further embodiment of any of the foregoing embodiments, the one or more different sensing parameters include an imaging resolution of the at least one sensor.

In a further embodiment of any of the foregoing embodiments, the one or more sensors include a first sensor and a second sensor. The processing circuitry is configured to use the first sensor to record the plurality of sensor readings, and move the first sensor relative to the component along a path to position the first sensor to record the plurality of sensor readings. The second sensor, which is separate from the first sensor, is used to record the additional sensor readings while the first sensor continues to follow the path.

In a further embodiment of any of the foregoing embodiments, the first and second sensors are both cameras.

In a further embodiment of any of the foregoing embodiments, one of the first and second sensors is a camera, and the other of the first and second sensors is a depth sensor, an ultrasonic sensor, or an x-ray imaging device.

In a further embodiment of any of the foregoing embodiments, the system includes a set of one or more robotic arms, a snake-arm robot, or a drone. The processing circuitry is configured to use said set of one or more robotic arms, said snake-arm robot, or said drone to move the first sensor relative to the component.

In a further embodiment of any of the foregoing embodiments, the one or more different sensing parameters include one or more of: a position of the sensor relative to the component, a distance between the sensor and the component, or an angle of the sensor relative to the component.

In a further embodiment of any of the foregoing embodiments, the one or more different sensing parameters include one or more of: a position of a light source relative to the component, an orientation of the light source relative to the component, or a brightness of the light source.

In a further embodiment of any of the foregoing embodiments, to update the nominal appearance metric, the processing circuitry is configured to calculate the nominal appearance metric based on the appearance metric of the particular sensor reading and M most recent sensor readings that precede the particular sensor reading.

The embodiments, examples, and alternatives of the preceding paragraphs, the claims, or the following description and drawings, including any of their various aspects or respective individual features, may be taken independently or in any combination. Features described in connection with one embodiment are applicable to all embodiments, unless such features are incompatible.

DETAILED DESCRIPTION

Figure 1A:
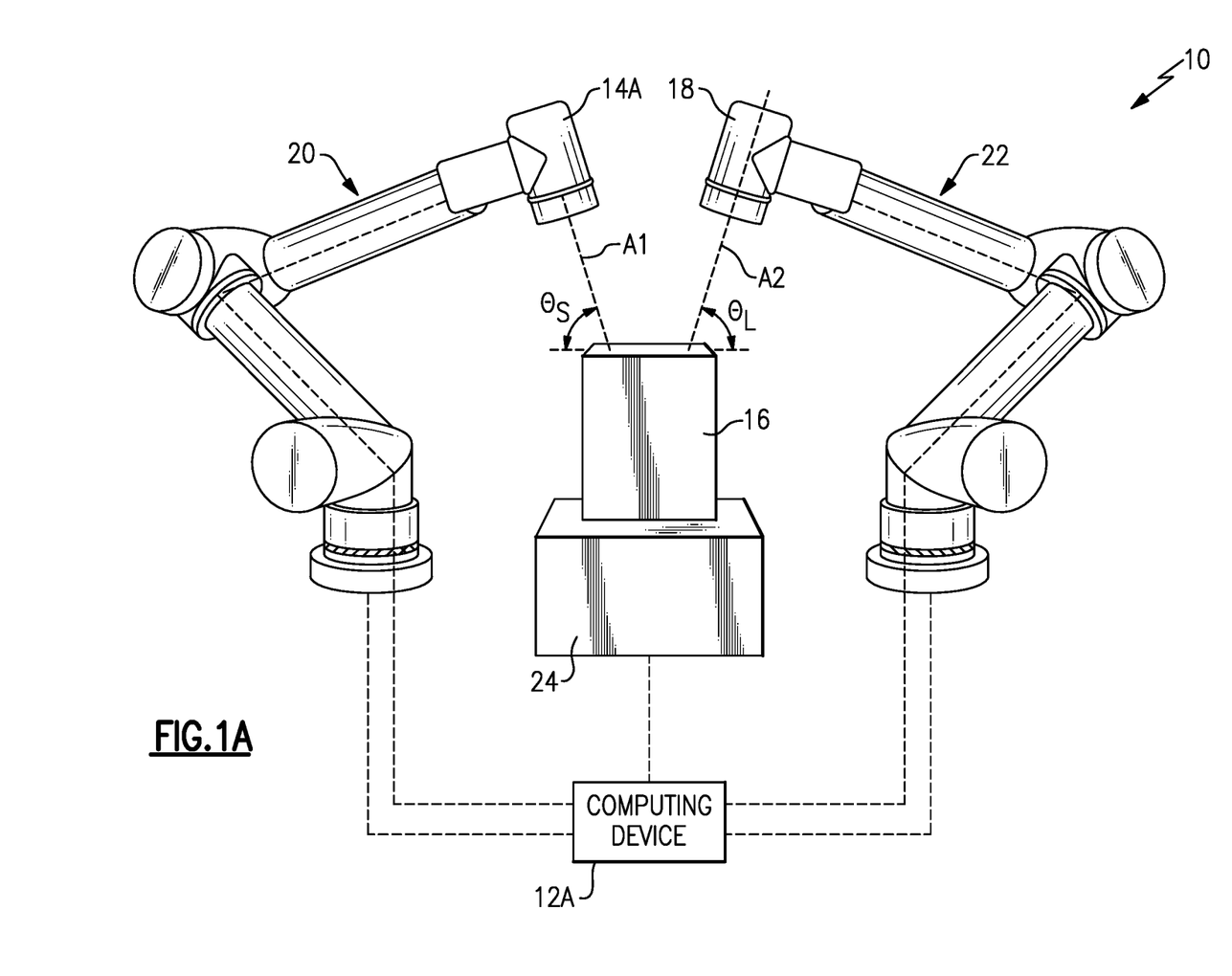
FIG. 1A schematically illustrates an example system for analyzing a component for anomalous regions, in which a sensor is mounted to one or more robotic arms.

FIG. 1A schematically illustrates an example system 10 for inspecting a component 16 for anomalous regions, which may be indicative of defects and/or degradation of the component 16 (e.g., scratches, cracks, dents, rust, voids in material, etc.). The system 10 includes a computing device 12 configured to utilize a sensor 14A to obtain sensor readings for the component 16. The sensor 14A may be a camera, a depth sensor (e.g., LIDAR or stereovision), an ultrasonic sensor, or an x-ray imaging device, for example. Optionally, the system 10 also includes a lighting device 18 configured to illuminate the component 16 for the sensor readings. In one non-limiting example, the component 16 is a component of a gas turbine engine, such as a turbine blade.

In the example of FIG. 1A, the sensor 14A is disposed at a distal end of a set of one or more robotic arms 20, and the lighting device 18 is disposed at a distal end of a set of one or more robotic arms 22. The sensor 14A has central longitudinal axis A1 (e.g., a camera optical axis) that intersects the component 16 at a sensor angle $\vartheta_s$ and the lighting device 18 has a central longitudinal axis A2 that intersects the component 16 at a lighting angle $\vartheta_L$.

The computing device 12A is configured to move the sensor 14A relative to the component 16 to record sensor data for different regions of the component 16. The computing device 12A may achieve this relative movement by actuating the set of robotic arms 20 and/or by moving an optional support 24 upon which the component 16 is disposed (e.g., by rotating the support 24).

In one example, the optional lighting device 18 is included, and the computing device 12A actuates the set of one or more robotic arms 22 to move the lighting device 18 to provide for different lighting conditions for the sensor 14A to record sensor readings.

Figure 1B:
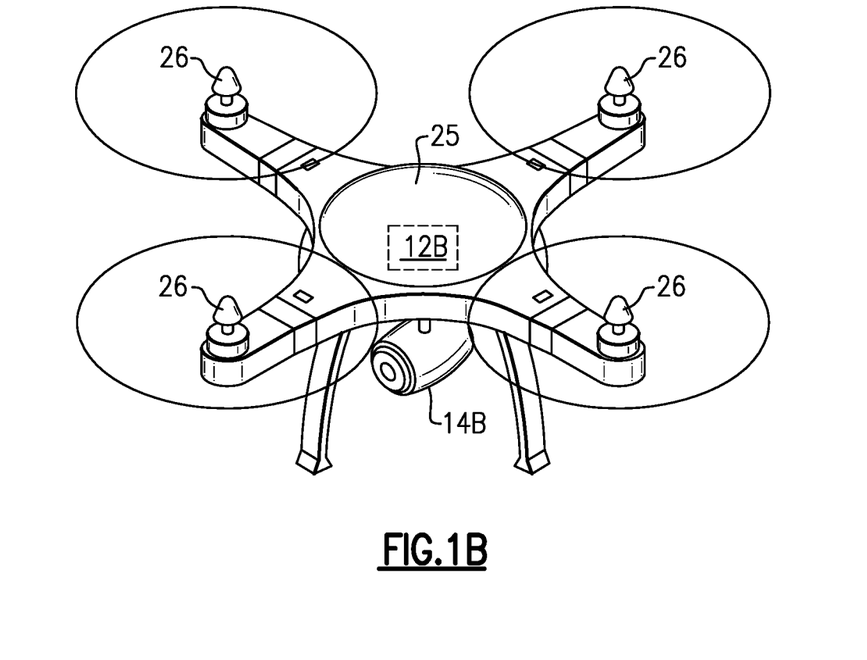
FIG. 1B schematically illustrates an example drone that may be used in the system of FIG. 1A.

FIG. 1B schematically illustrates an example drone 25 that may be used in the system of FIG. 1A (e.g., in addition to, or in place of the set of one or more robotic arms 20 and/or set of one or more robotic arms 22). The drone 25 includes a computing device 12B that controls movement of a sensor 14B relative to the component 16 independently of and/or in conjunction with movement of the drone 25. The computing device 12B also controls operation of a plurality of rotors 26 to control movement of the drone 25, which, as discussed above, may also cause movement of the sensor 14B. Although four rotors 26 are shown, it is understood that other quantities could be used.

Figure 1C:
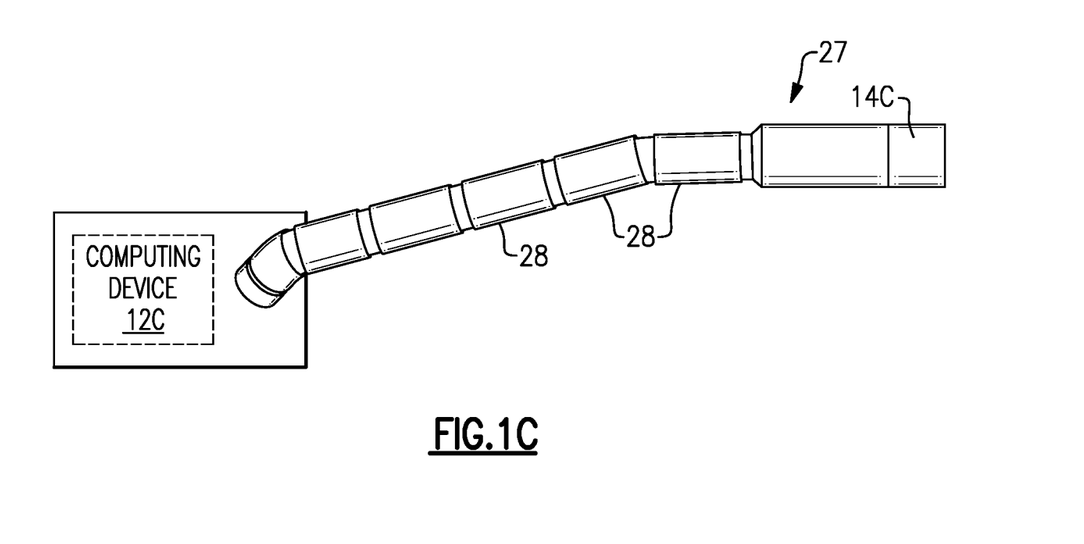
FIG. 1C schematically illustrates an example snake-arm robot that may be used in the system of FIG. 1A.

FIG. 1C schematically illustrates an example snake-arm robot 27 that may be used in the system of FIG. 1A (e.g., in addition to, or in place of the set of one or more robotic arms 20 and/or the set of one or more robotic arms 22). The snake-arm robot 27 includes a computing device 12C that controls movement of a plurality of mechanical linkages 28 in order to control movement of a sensor 14C relative to the component 16.

Although not shown in FIG. 1B or 1C, it is understood that the lighting device 18 may be included, and if included may, for example, be secured to the drone 25, the snake-arm robot 27, or the set of one or more robotic arms 22. In one example, both the sensor 14 and the lighting device 25 are attached to a same set of robotic arms 20, a same drone 25, or a same snake-arm robot 27.

In this disclosure, reference numeral 14 will be generically used to refer to the sensors 14A-C, and reference numeral 12 will be generally used to refer to the computing devices 12A-C. Unless otherwise indicated below, any use of numerals 14 and 16 can refer to any of the embodiments of FIGS. 1A-C.

Figure 2:
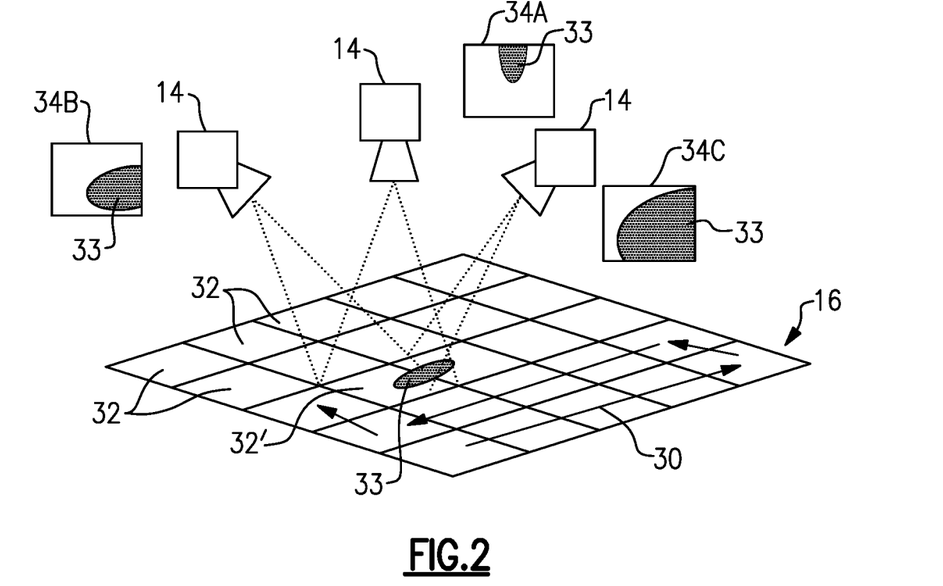
FIG. 2 schematically illustrates a path of relative movement between a sensor and a component.

FIG. 2 schematically illustrates a path 30 of relative movement between the sensor 14 and the component 16. The computing device 12 is configured to move the sensor 14 along the example path 30 relative to the component 16 to record a plurality of sensor readings of the component 16. In the example of FIG. 2, a sensor reading is recorded for each of a plurality of regions 32 of the component 16. The path 30 may be a predefined path based on a computer model of the component 16 that is stored in memory of the computing device 12, for example.

As will be discussed below in greater detail, the computing device 12 is configured to determine an appearance metric for a particular one of the sensor readings, and compare that metric to an aggregate, nominal appearance metric for preceding ones of the sensors readings (and discussed below in greater detail). If a difference between the metrics exceeds a threshold, the computing device 12 determines that the particular sensor reading depicts an anomalous region, and records additional sensor readings of the anomalous region using one or more sensing parameters that differ from those used to record the anomalous sensor reading, in order to gain additional insight into the anomalous region. Each appearance metric represents a high-level statistical characterization of its associated depicted region 32.

In FIG. 2, region 32' is an anomalous region because it includes a darkened area 33 that is substantially darker than the neighboring regions 32. A first sensor reading 34A is shown corresponding to a first view of the anomalous region 32 (e.g., with a sensor angle $\vartheta_s$ of approximately 90°). If the sensor reading is a photographic image, the darkened area 33 is likely to cause certain appearance metrics, such as, in the example of a camera sensor, average sensor value (e.g., average pixel value), sensor value gradient (e.g., pixel value gradient), and/or edge detection/circle detection to differ from the preceding images (e.g., differ from a certain number of preceding images and/or differ from an average value of a certain number of preceding images).

In the example of a LIDAR sensor, the metric may indicate an intensity or distance traveled of a LIDAR return beam, for example. In the example of an ultrasonic sensor, the metric may indicate an intensity of a sound beam reflected from within a defect in the part for pulse echo ultrasonic, and/or an intensity of a sound beam emanating from another side of the part in a through transmission ultrasonic. A similar concept may apply for x-rays where the metric could include x-ray signal attenuation.

Based on the difference between the metric and the nominal appearance metric (discussed above), the computing device 12 controls the sensor 14 and/or the lighting device 18 to record additional sensor readings 34B and 34C of the anomalous region 32' using one or more sensing parameters that differ from those used to record the initial anomalous sensor reading 34A. The additional sensor readings may offer further insight or greater visibility of the potential defect and/or degradation through this variation of parameters.

The computing device 12 may be driven by information theoretic and/or curiosity-based principles in its exploration of a candidate region of interest to gain insight into a potential defect and/or degradation through the capture of dissimilar sensor readings based on the idea that dissimilar sensor readings of the same region likely offer different insights. These dissimilar sensor readings can be captured through varying sensing parameters such as viewing angle, zoom, and lighting conditions. By varying these parameters, more dissimilar images, each providing unique insight, can be obtained efficiently.

In an example where the sensor 14 is a camera, some non-limiting examples of differing sensing parameters (which in this example would be photographic parameters) that may be used for a particular sensor reading (in this example a particular image) as compared to a preceding sensor reading may include one or any combination of the following, for example:
  different camera 14 position relative to the component 16,
  different camera 14 orientation relative to the component 16, as indicated by the sensor angle $\vartheta_s$, which in this example would be a camera angle,
  different lighting device 18 location relative to the component 16,
  different lighting device 18 orientation relative to the component 16, as indicated by the lighting angle $\vartheta_L$,
  different lighting source 18 brightness, and/or
  different image resolution.

As discussed above, a camera is a non-limiting example, and other sensors could be used such as a depth sensor (e.g., LIDAR or stereovision), an ultrasonic sensor, and/or an x-ray imaging device, for example. Some sensing parameters that may be used for a particular sensor reading (for cameras or non-camera sensors) could include any one or combination of the following, for example:
  a distance between the sensor 14 and the component 16,
  the sensor angle $\vartheta_s$ with respect to the component 16, and/or
  a position of the sensor 14 with respect to the component 16.

Figure 3:
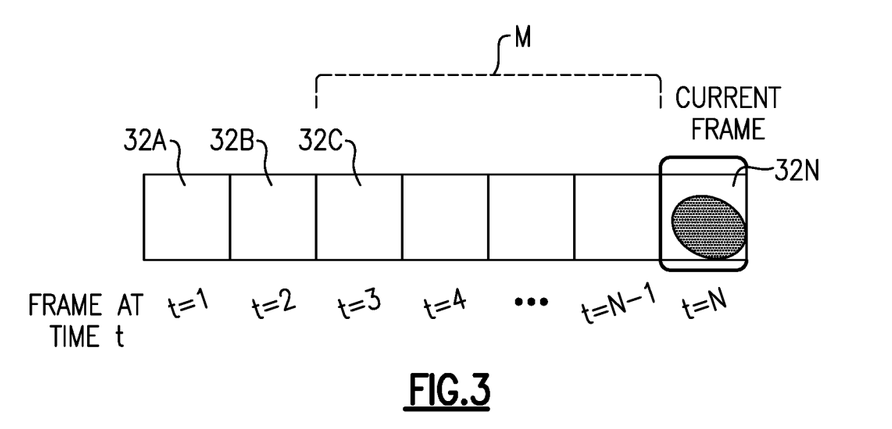
FIG. 3 schematically illustrates movement of a sensor relative to a component.

FIG. 3 schematically illustrates movement of the sensor 14 relative to the component 16. A plurality of neighboring regions 32 are shown, each of which are recorded in a separate sensor reading. Thus, a first sensor reading of region 32A is recorded at time t=1, a second sensor reading of region 32B is recorded at time t=2, a third sensor reading of region 32C is recorded at time t=3, and so on, until a sensor reading of region 32N is recorded at time t=N. In one example, the nominal appearance metric is calculated based on the sensor readings of the M neighboring regions that precede region 32N and/or the M most recent sensor readings.

If a short-term memory window used for the preceding M images to determine the nominal appearance metric is relatively small, the nominal appearance metric is likely to be contextually appropriate, and to support anomaly detection that is adaptive and robust to changes in part surface characteristics, defect type, and environmental conditions.

The window M may be adjusted based on a number of factors. For example, if the component features a repetitive surface pattern, the computing device 12 may be configured so that the window includes an entire unit of the pattern, so that the pattern itself is not interpreted as an anomaly. The window may also be adjusted adaptively by using change detection techniques, e.g., looking at the trends of how the metric is statistically changing over the window and identifying a point where there is large enough change which determines the end point of the window.

Figure 4:
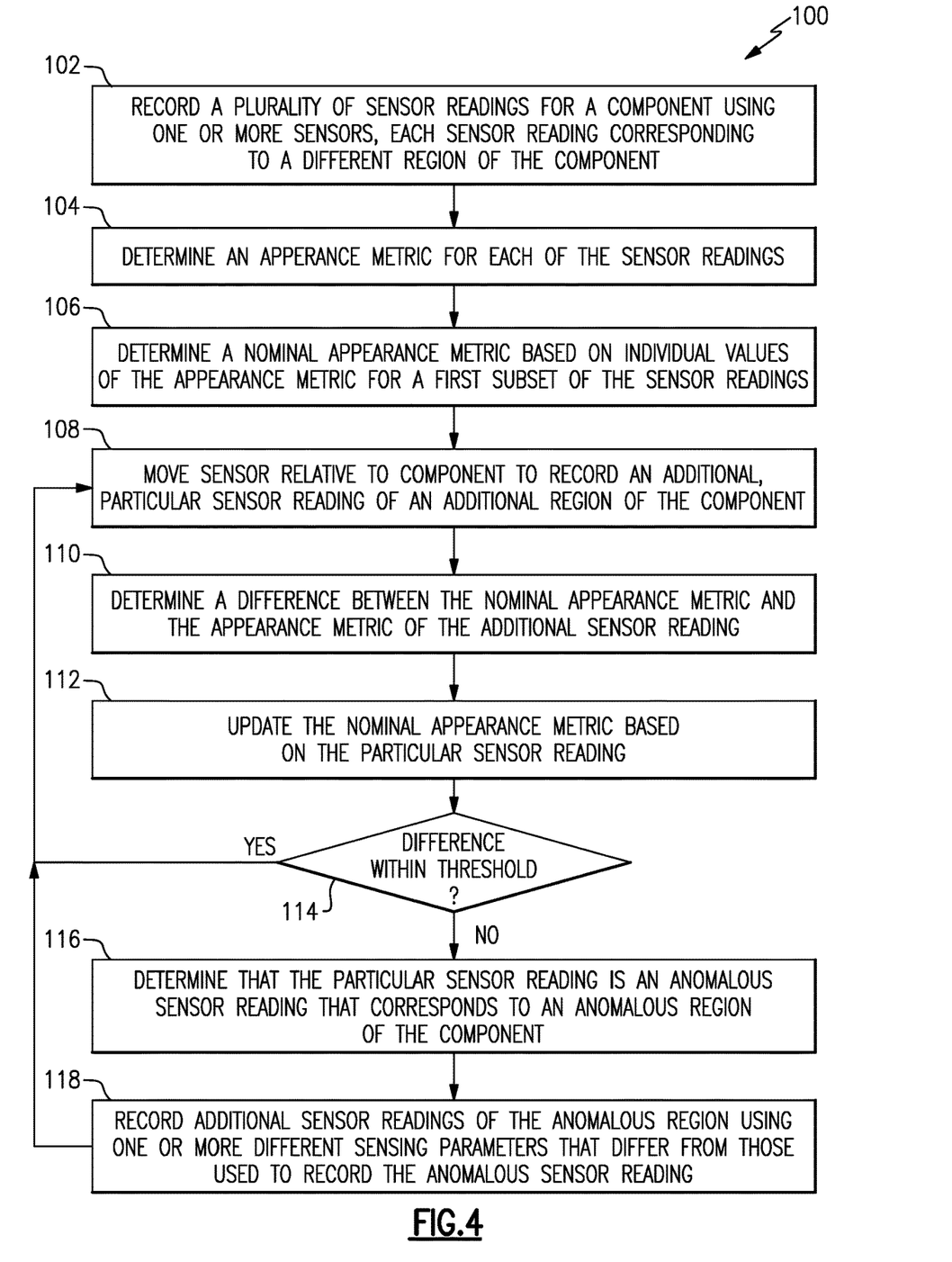
FIG. 4 is a flowchart of an example method of analyzing a component for anomalous regions.

FIG. 4 is a flowchart of an example method 100 of inspecting a component 16 for anomalous regions. A plurality of sensor readings (e.g., images 34) of the component 16 are recorded using one or more sensors 14 (step 102), with each sensor reading corresponding to a different region 32 of the component 16. An appearance metric is determined for each of the sensor readings (step 104). The appearance metric may be an average sensor value (e.g., average pixel value), a sensor value gradient (e.g., pixel value gradient), or various low-level detected features such as edges, corners, and/or circles, for example. In one example, where the sensor 14 is a depth sensor, the sensor data may be voxelized and characterized through determination of number of surfaces, centroids, etc.

A nominal appearance metric is determined based on individual values of the appearance metric for a first subset of the sensor readings (step 106) (e.g., the M preceding sensor readings as discussed in connection with FIG. 3). The nominal appearance metric may be an average of the individual values, for example. The appearance metric may be defined by a human expert, or may be learned automatically using deep learning methods, for example.

The sensor 14 is moved relative to the component 16 to record an additional, particular sensor reading of an additional region 32 (step 108). Moving the sensor 14 relative to the component 16 may include using the set of one or more robotic arms 20, for example. Alternatively, if the camera 14 is a part of a snake-arm robot or secured to a drone, then the snake-arm robot or drone could be used to provide the movement of the camera 14 relative to the component 16.

A difference is determined between the nominal appearance metric and the appearance metric of the particular sensor reading 34 (step 110). The nominal appearance metric is updated based on the particular sensor reading (step 112). In one example, the updating of step 112 includes recalculating the nominal appearance metric based only on the preceding M sensor readings, so that sensor readings before the earliest of the M sensor readings are excluded from the updated determination of the nominal appearance metric.

The difference determined in step 110 is compared to a threshold (step 114). If the difference is within the threshold (a "yes" to step 114), the method proceeds back to step 108 for another iteration. The threshold may be fixed or adaptive. In one example that utilizes an adaptive threshold for comparison in step 114, the threshold is lowered based on an anomalous area detection rate being below a first detection threshold (e.g., corresponding to a first detection rate, below which false negative detections may be likely) and/or is raised based on an anomalous detection rate being above a second detection threshold (e.g., corresponding to a second detection rate, above which false positive detections may be likely).

If the difference exceeds the threshold (a "no" to step 114), a determination is made that the particular sensor reading is an anomalous sensor reading that corresponds to an anomalous region of the component (step 116), and additional sensor readings of the anomalous region are recorded using one or more sensing parameters that differ from those used to record the anomalous sensor reading (step 118). Steps 108-118 are then iteratively repeated to continue inspecting the component 16.

In one example, the quantity of additional sensor readings that are recorded in step 118 depends on a magnitude of the difference determined in step 110. In one example, as the difference increases, the quantity of additional sensor readings also increases. In another example, as the different increases, the quantity of additional sensor readings decreases. Thus, the magnitude of the difference determined in step 110 may be used to control the exploration strategy of the component 16.

In one example, a second sensor that is different from the first sensor 14 is used to record the additional sensor readings (e.g., additional images) of the anomalous area in step 118 while the first sensor 14 continues to traverse the path and record sensor readings of regions 32 of the component 16 that have not yet been assessed for whether they are anomalous. Thus, the system 10 may be a multi-agent system, where a first sensor 14 identifies anomalous regions, and a second sensor 14 explores them. As used above, the sensors being "different" from each other may mean that they are separate, but are a same type of sensor (e.g., both cameras), or are separate and are also different types of sensors (e.g., one is a camera, and one is a LIDAR sensor, ultrasonic sensor, or x-ray imaging device, for example). In one example, the sensors 14 each explore the component 16 independently and explore the anomalous regions they respectively identify.

In one example, in conjunction with step 118, based on detection of an anomalous region, the computing device 12 assesses the sensor readings to determine what type of anomaly is detected. This may include one or any combination of the following, for example: comparison against template/reference images, analyzing detected features, such as edges, and/or utilizing a neural network (e.g., that has been trained with historical sensor readings for anomalies and/or specific types of defects).

The method 100 provides for a generalized determination of anomalous regions to support defect detection and identification that is robust to variation in lighting conditions, part surface characteristics, or defect appearance that would limit the usefulness of predefined models or libraries of features for defect detection. Through a high-level statistical characterization of a currently-viewed region, and comparison of this characterization with a short-term memory window including the average characterization of some number of neighboring, previously-viewed regions, a determination can be made as to whether the currently-viewed region is anomalous.

The short-term memory window may be frequently updated, ensuring that the nominal appearance metric is contextually-appropriate. This supports anomaly detection that is adaptive and robust to changes in part surface characteristics, defect type, and environmental conditions.

The method 100 provides for an enhanced, robot-enabled automated visual inspection through exploratory selective capture of additional sensor readings of anomalous, and potentially defect-containing, regions. Because anomalous regions may be identified based on sensor readings (e.g., images) of neighboring regions, differences between similar sensor readings can be used to identify anomalous regions, instead of relying on rigid definitions of potential defects, which may be limited to a relatively small amount of defect types and/or which may rely on sensor readings that were recorded under photographic and/or environmental conditions that differ from the system 10. For example, an image of a damaged turbine blade in a bright laboratory setting may look substantially different from an image of the same damaged component taken with a snake-arm robot inserted into a gas turbine engine. Thus, a highly-controlled sensing (e.g., photographic) environment is not required to get good results from the method 100.

The method 100 enables the selective deployment of additional sensing/processing resources, focusing their use in regions that have been identified as anomalous and, as such, more likely to contain a defect. This allows for generalized, efficient, and enhanced data collection to support automated inspection processes through the targeted use of sensing resources that would be very costly in time, memory, and computational resources if applied indiscriminately in a blanket manner (e.g., requiring multiple camera angles and multiple lighting angles for inspection of every region of a component, including non-anomalous regions). Using the method 100, any anomaly can be flagged for selective, enhanced inspection, offering versatility and efficiency over approaches relying on a fixed set of defect classes or blanket use of resources. The method 100 is agile, robust, and rapidly re-deployable, and in a manner that improves confidence in defect detection.

Although example embodiments have been disclosed, a worker of ordinary skill in this art would recognize that certain modifications would come within the scope of this disclosure. For that reason, the following claims should be studied to determine the scope and content of this disclosure.

What is claimed is:

1. A method of inspecting a component for anomalous regions, comprising:
    recording a plurality of sensor readings for a component using one or more sensors, each sensor reading corresponding to a different region of the component, wherein the component is a turbine blade of a gas turbine engine;
    determining an appearance metric for each of the sensor readings;

determining a nominal appearance metric based on individual values of the appearance metric for a first subset of the sensor readings, wherein the first subset of the sensor readings includes some but not all of the sensor readings; and for a particular sensor reading of the plurality of sensor readings that is outside of the first subset:
determining a difference between the nominal appearance metric and the appearance metric of the particular sensor reading;
updating the nominal appearance metric based on the particular sensor reading; and
based on the difference exceeding a threshold, determining that the particular sensor reading is an anomalous sensor reading that corresponds to an anomalous region of the component, and recording additional sensor readings of the anomalous region using one or more different sensing parameters that differ from those used to record the anomalous sensor reading wherein the one or more sensors include a first sensor and a second sensor; and wherein said recording a plurality of sensor readings is performed using the first sensor, and the method comprises:
moving the first sensor relative to the component along a path to position the first sensor for said recording a plurality of sensor readings; and
using a second sensor, which is separate from the first sensor, for said recording additional sensor readings while the first sensor continues to follow the path.

2. The method of claim 1, wherein the one or more sensors include a camera.

3. The method of claim 1, wherein the one or more different sensing parameters include an imaging resolution of the at least one sensor.

4. The method of claim 1, wherein the first and second sensors are both cameras.

5. The method of claim 1, wherein one of the first and second sensors is a camera, and the other of the first and second sensors is a LIDAR sensor, an ultrasonic sensor, or an x-ray imaging device.

6. The method of claim 1, wherein said moving the first sensor relative to the component comprises using a set of one or more robotic arms, a snake-arm robot, or a drone to move the first sensor relative to the component.

7. The method of claim 1, wherein the one or more different sensing parameters include one or more of:
a position of the sensor relative to the component;
a distance between the sensor and the component; or
an angle of the sensor relative to the component.

8. The method of claim 1, wherein the one or more different sensing parameters includes one or more of: a position of a light source relative to the component, an orientation of the light source relative to the component, or a brightness of the light source.

9. The method of claim 1, wherein M is an integer, and wherein said updating the nominal appearance metric comprises calculating the nominal appearance metric based on the appearance metric of the particular sensor reading and M most recent sensor readings that precede the particular sensor reading.

10. A system for inspecting a component for anomalous regions, comprising:
one or more sensors; and
processing circuitry configured to:
record a plurality of sensor readings for a component using the one or more sensors, each sensor reading corresponding to a different region of the component, wherein the component is a turbine blade of a gas turbine engine;
determine an appearance metric for each of the sensor readings;
determine a nominal appearance metric based on individual values of the appearance metric for a first subset of the sensor readings, wherein the first subset of the sensor readings includes some but not all of the sensor readings; and
for a particular sensor reading of the plurality of sensor readings that is outside of the first subset:
determine a difference between the nominal appearance metric and the appearance metric of the particular sensor reading;
update the nominal appearance metric based on the particular sensor reading; and
based on the difference exceeding a threshold, determine that the particular sensor reading is an anomalous sensor reading that corresponds to an anomalous region of the component, and record additional sensor readings of the anomalous region using one or more different sensing parameters that differ from those used to record the anomalous sensor reading;

wherein the one or more sensors include a first sensor and a second sensor; and wherein the processing circuitry is configured to:
use the first sensor to record the plurality of sensor readings, and move the first sensor relative to the component along a path to position the first sensor to record the plurality of sensor readings;
wherein the second sensor, which is separate from the first sensor, is used to record the additional sensor readings while the first sensor continues to follow the path.

11. The system of claim 10, wherein the one or more sensors include a camera.

12. The system of claim 10, wherein the one or more different sensing parameters include an imaging resolution of the at least one sensor.

13. The system of claim 10, wherein the first and second sensors are both cameras.

14. The system of claim 10, wherein one of the first and second sensors is a camera, and the other of the first and second sensors is a LIDAR sensor, an ultrasonic sensor, or an x-ray imaging device.

15. The system of claim 12, including:
a set of one or more robotic arms, a snake-arm robot, or a drone;
wherein the processing circuitry is configured to use said set of one or more robotic arms, said snake-arm robot, or said drone to move the first sensor relative to the component.

16. The system of claim 10, wherein the one or more different sensing parameters include one or more of:
a position of the sensor relative to the component;
a distance between the sensor and the component; or
an angle of the sensor relative to the component.

17. The system of claim 10, wherein the one or more different sensing parameters includes one or more of: a position of a light source relative to the component, an orientation of the light source relative to the component, or a brightness of the light source.

18. The system of claim 10, wherein M is an integer, and wherein to update the nominal appearance metric, the processing circuitry is configured to calculate the nominal appearance metric based on the appearance metric of the particular sensor reading and M most recent sensor readings that precede the particular sensor reading.

19. The method of claim 5, wherein the other of the first and second sensors is a LIDAR sensor.

20. The method of claim 5, wherein the other of the first and second sensors is an ultrasonic sensor.

21. The method of claim 5, wherein the other of the first and second sensors is an x-ray imaging device.

22. The system of claim 14, wherein the other of the first and second sensors is a LIDAR sensor.

23. The system of claim 14, wherein the other of the first and second sensors is an ultrasonic sensor.

24. The system of claim 14, wherein the other of the first and second sensors is an x-ray imaging device.

* * * * *